(12) United States Patent
Takekoshi (10) Patent No.: US 7,826,591 B2
(45) Date of Patent: Nov. 2, 2010

(54) X-RAY IMAGING APPARATUS AND X-RAY IMAGING METHOD

(75) Inventor: Koji Takekoshi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/607,658

(22) Filed: Oct. 28, 2009

(65) Prior Publication Data

US 2010/0111257 A1    May 6, 2010

(30) Foreign Application Priority Data

Oct. 30, 2008    (JP) .............................. 2008-279827

(51) Int. Cl.
    *G01N 23/04*    (2006.01)
(52) U.S. Cl. ....................................... 378/62
(58) Field of Classification Search ................... 378/62, 378/114, 901; 382/131, 132
    See application file for complete search history.

(56) References Cited

FOREIGN PATENT DOCUMENTS

| JP | 5-064081 A | 3/1993 |
| JP | 3066944 B2 | 5/1996 |
| JP | 2007-222312 A | 9/2007 |

*Primary Examiner*—Courtney Thomas
(74) *Attorney, Agent, or Firm*—Canon U.S.A., Inc., IP Division (57) ABSTRACT

An X-ray generation unit for generating X-rays, an X-ray imaging unit for performing X-ray imaging, and an X-ray imaging control unit for controlling X-ray imaging communicate information with one another via a communication line, to pick up a medical X-ray image. The X-ray generation unit receives X-ray imaging permission from the X-ray imaging control unit, and the X-ray imaging unit receives the X-ray imaging permission from the X-ray imaging control unit. The X-ray imaging control unit includes an X-ray imaging permission transmission unit for transmitting the X-ray imaging permission to the X-ray generation unit and the X-ray imaging unit, an X-ray imaging permission reception unit, an imaging condition determination unit for determining an imaging condition from an imaging order, an imaging permission condition determination unit for determining an imaging permission condition from the determined imaging condition, and a processing control unit for performing processing according to the imaging permission condition determined by the imaging permission condition determination unit.

16 Claims, 11 Drawing Sheets

STILL IMAGE PICKUP

FIG. 7B

RADIOSCOPY
STILL IMAGE PICKUP

FIG. 7C

CINERADIOGRAPHY
RADIOSCOPY
STILL IMAGE PICKUP

FIG. 7D

| IMAGING ORDER | IMAGING PROCESSING LOAD |
|---|---|
| RADIOSCOPY EXISTS | 10 |
| CINERADIOGRAPHY EXISTS | 10 |
| STILL IMAGE EXISTS | 1 |
| DSA EXISTS | 10 |
| ... | ... |

FIG. 8

| IMAGING MODE | IMAGING CONDITIONS ||| IMAGING PROCESSING LOAD | POST-IMAGING PROCESSING LOAD |
| --- | --- | --- | --- | --- | --- |
| | FRAME RATE | READING SIZE | PIXEL ADDITION | | |
| RADIOSCOPY | 30fps | 17"×14" | 1×1 | 10 | 3 |
| RADIOSCOPY | 30fps | 12"×12" | 1×1 | 10 | 2 |
| RADIOSCOPY | 30fps | 9"×9" | 1×1 | 10 | 1 |
| RADIOSCOPY | 30fps | 17"×14" | 2×2 | 10 | 3 |
| RADIOSCOPY | 30fps | 12"×12" | 2×2 | 10 | 2 |
| RADIOSCOPY | 30fps | 9"×9" | 2×2 | 10 | 1 |
| ⋮ | ⋮ | ⋮ | ⋮ | ⋮ | ⋮ |
| CINERADIOGRAPHY | 30fps | 9"×9" | 2×2 | 10 | 8 |
| CINERADIOGRAPHY | 15fps | 12"×12" | 2×2 | 8 | 8 |
| CINERADIOGRAPHY | 15fps | 9"×9" | 2×2 | 6 | 7 |
| CINERADIOGRAPHY | 10fps | 17"×14" | 2×2 | 10 | 5 |
| CINERADIOGRAPHY | 10fps | 12"×12" | 2×2 | 10 | 5 |
| CINERADIOGRAPHY | 10fps | 9"×9" | 2×2 | 10 | 5 |
| ⋮ | ⋮ | ⋮ | ⋮ | ⋮ | ⋮ |
| STILL IMAGE | — | 17"×14" | 1×1 | 3 | 1 |
| STILL IMAGE | — | 12"×12" | 1×1 | 3 | 1 |
| STILL IMAGE | — | 9"×9" | 1×1 | 3 | 1 |

FIG. 9A

| FRAME RATE | INDEX |
|---|---|
| 30fps | 10 |
| 20fps | 8 |
| 10fps | 6 |
| 5fps | 4 |
| 2.5 fps OR LESS | 2 |
| STILL IMAGE | 1 |

| READING SIZE | INDEX |
|---|---|
| 17" × 14" | 5 |
| 12" × 12" | 3 |
| 9" × 9" | 1 |

| PIXEL ADDITION | INDEX |
|---|---|
| 1 × 1 | 4 |
| 2 × 2 | 1 |

= IMAGING PROCESSING LOAD

FIG. 10A

IMAGE SIZE × | NUMBER OF IMAGES TO BE PROCESSED | ×

FIG. 10B

| TYPE OF POST-IMAGING PROCESSING | INDEX |
|---|---|
| DICOM STORAGE TRANSFER | 0.5 |
| DICOM PRINT TRANSFER | 0.6 |
| STORAGE COMMIT PROCESSING | 0.1 |
| MPPS NOTIFICATION | 0.1 |
| GSPS OBJECT GENERATION | 0.3 |
| DICOM DISK STORAGE | 0.4 |
| IMAGE PROCESSING | 0.3 |
| STORAGE PROCESSING | 0.1 |

= POST-IMAGING PROCESSING LOAD

FIG. 11

X-RAY IMAGING APPARATUS AND X-RAY IMAGING METHOD

BACKGROUND OF THE INVENTION

1. Field of the Invention

The present invention relates to an X-ray imaging apparatus and an X-ray imaging method for performing X-ray imaging.

2. Description of the Related Art

In recent years, a high-resolution solid-state X-ray detector using a flat panel detector (FPD) has been proposed. Japanese Patent No. 3,066,944 discusses a method for placing an object between an X-ray source and an X-ray sensor and converting a dose of X-rays that have passed through the object into an electrical signal to obtain an X-ray image of the object as digital data.

Japanese Patent Application Laid-Open No. 5-064081 discusses an X-ray television (TV) apparatus that performs radioscopic imaging for displaying an X-ray radiographic image on a cathode ray tube (CRT) using an image intensifier (I. I).

Japanese Patent Application Laid-Open No. 2007-222312 discusses, for a technique for processing a request for image transfer between a primary storage unit for temporarily storing an image in an X-ray imaging unit and a secondary storage unit for permanently storing an image, an improvement in the response to an operator's instruction by switching the priority order of processes depending on the situation.

The basic processing flow of medical image pickup includes processing steps for performing imaging with imaging conditions specified by an imaging order, and outputting a picked-up image. More specifically, the processing flow can be classified into pre-imaging processing, imaging processing, and post-imaging processing. The imaging processing is required to display an image immediately after imaging, and therefore requires real-time properties, while the post-imaging processing does not require real-time properties.

The post-imaging processing includes processing for outputting a film output of an image, processing for transferring an image to an image server or an image viewer, and processing for storing an image in a local hard disk.

The post-imaging processing does not require interactive processing with an operator. Therefore, it is considered that post-imaging processing is performed in the background so that an operator performs imaging successively. Such a method for performing processing in the background can be achieved by a general known technique.

When the imaging processing and the post-imaging processing are performed in parallel, however, the post-imaging processing consumes large amounts of processing resources of a processing apparatus. This reduces the processing efficiency of the imaging processing requiring the real-time properties, resulting in a delay in the imaging processing and image data missing from reception.

On the other hand, when the imaging processing cannot be performed during the post-imaging processing, the operator cannot perform the imaging until the post-imaging processing is terminated, making working efficiency less efficient.

SUMMARY OF THE INVENTION

The present invention is directed to an X-ray imaging apparatus and an X-ray imaging method, which enable working efficiency to be improved by performing post-imaging processing while ensuring imaging processing in real time.

According to an aspect of the present invention, an X-ray imaging apparatus including an X-ray imaging unit configured to acquire an X-ray image by imaging using X-rays generated by an X-ray generation unit includes a post-imaging processing unit configured to perform post-imaging processing for the X-ray image acquired by the X-ray imaging unit, a determination unit configured to determine in real time whether an imaging order for the X-ray image is received, and a control unit configured to cause the post-imaging processing unit to perform the post-imaging processing when the determination unit does not determine that the imaging order for the X-ray image is received, while causing the post-imaging processing unit to stop the post-imaging processing and then permitting the imaging of the X-rays by the imaging order when the determination unit determines that the imaging order for the X-ray image is received and the post-imaging processing unit is performing the post-imaging processing.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
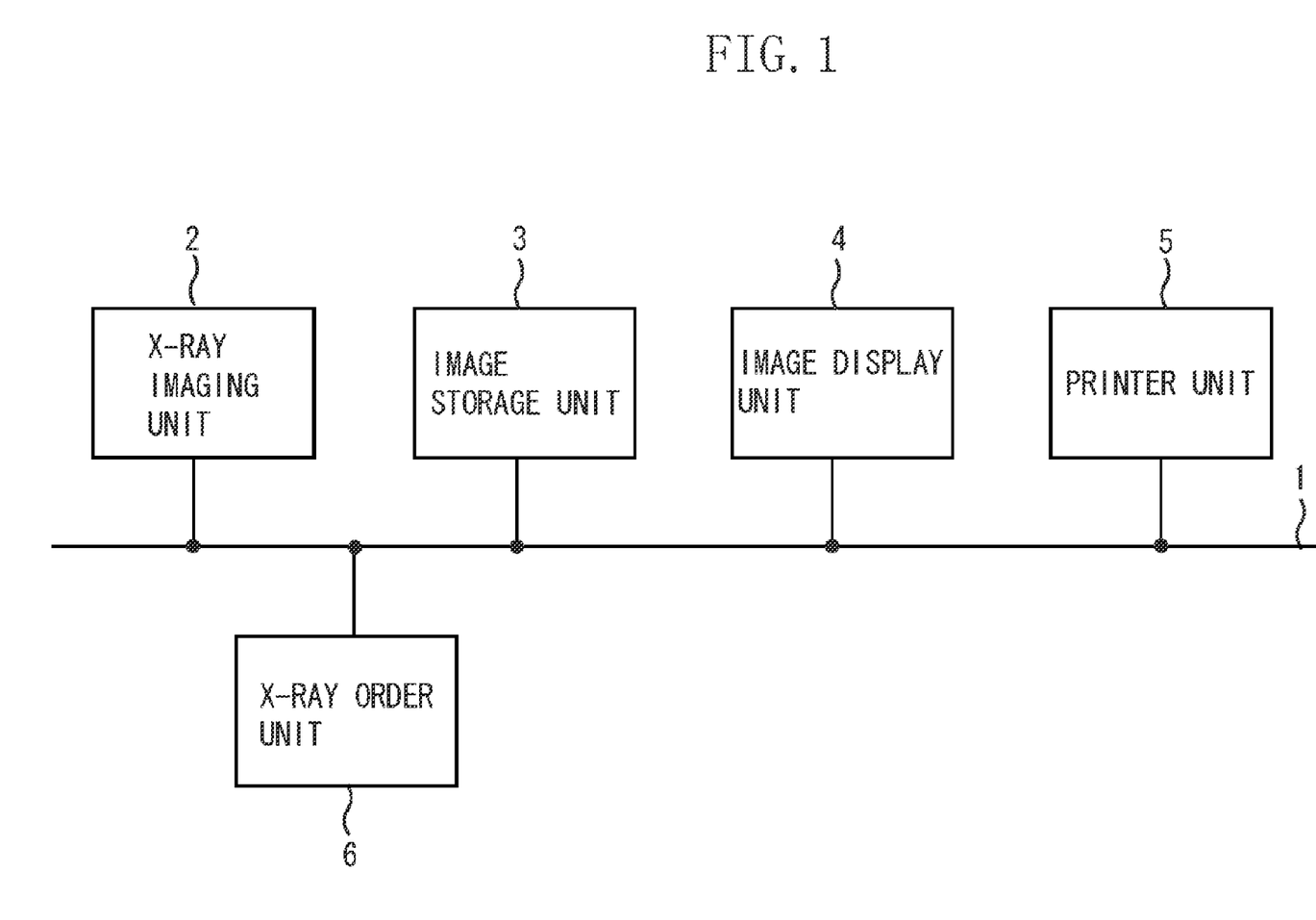
FIG. 1 is a block diagram illustrating a system configuration according to a first exemplary embodiment.

FIG. 1 is a system configuration diagram according to a first exemplary embodiment. An X-ray imaging unit 2, an image storage unit 3, an image display unit 4, a printer unit 5, and an X-ray order unit 6 are connected to one another via a communication circuit by a network 1. The X-ray imaging unit 2 is represented by X-ray computed tomography (CT) or a magnetic resonance imaging (MRI) apparatus for performing X-ray imaging, and is also referred to as modality.

The image storage unit 3 stores a medical X-ray image captured by the X-ray imaging unit 2, and is also referred to as picture archiving and communications systems (PACS). The image display unit 4 displays an image for image diagnosis, and the printer unit 5 prints an X-ray image on a film or paper. However, the printer unit 5 may not be provided in case of filmless operation.

The X-ray order unit 6 gives an imaging order, and is also referred to as radiology information systems (RIS).

Figure 2:
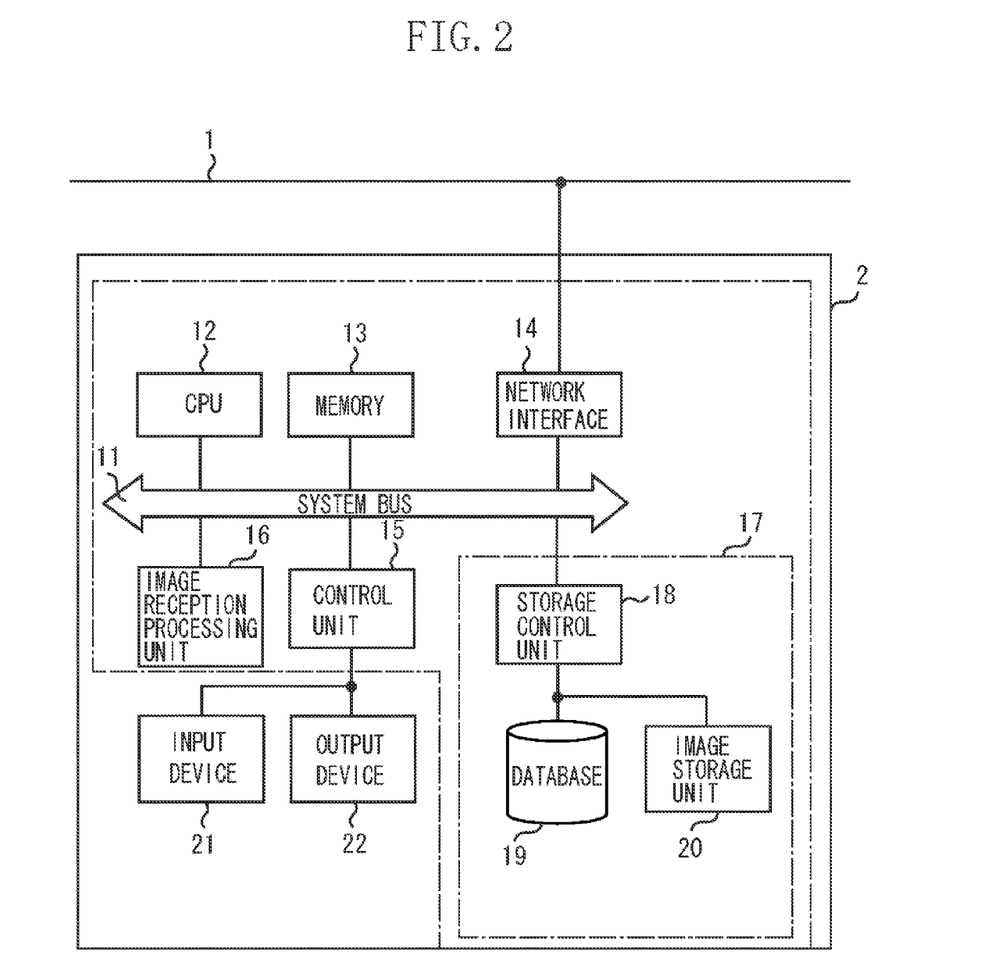
FIG. 2 is a block circuit diagram of a computer system.

FIG. 2 is a block circuit diagram of an X-ray imaging apparatus including a large scale integrated circuit (LSI) or an application specific integrated circuit (ASIC), for example, illustrating a computer system for executing a program. A central processing unit (CPU) 12, a memory 13, a network interface 14, a control unit 15, an image reception processing unit 16 for performing image reception processing of an X-ray image, and a storage device 17 are connected so as to be able to communicate with one another via a system bus 11 within the X-ray imaging unit 2.

The network interface 14 is connected to the network 1. A data base 19 storing patient information and image information and an image storage unit 20 storing image data are connected to a storage control unit 18 in the storage device 17. Furthermore, an input device 21 and an output device 22 are connected to the control unit 15.

In this computer system, examples of a processing resource include a data communication band resource, a CPU resource, a ground power unit (GPU) processing resource, a hard disk writing resource, and a network resource.

Figure 3:
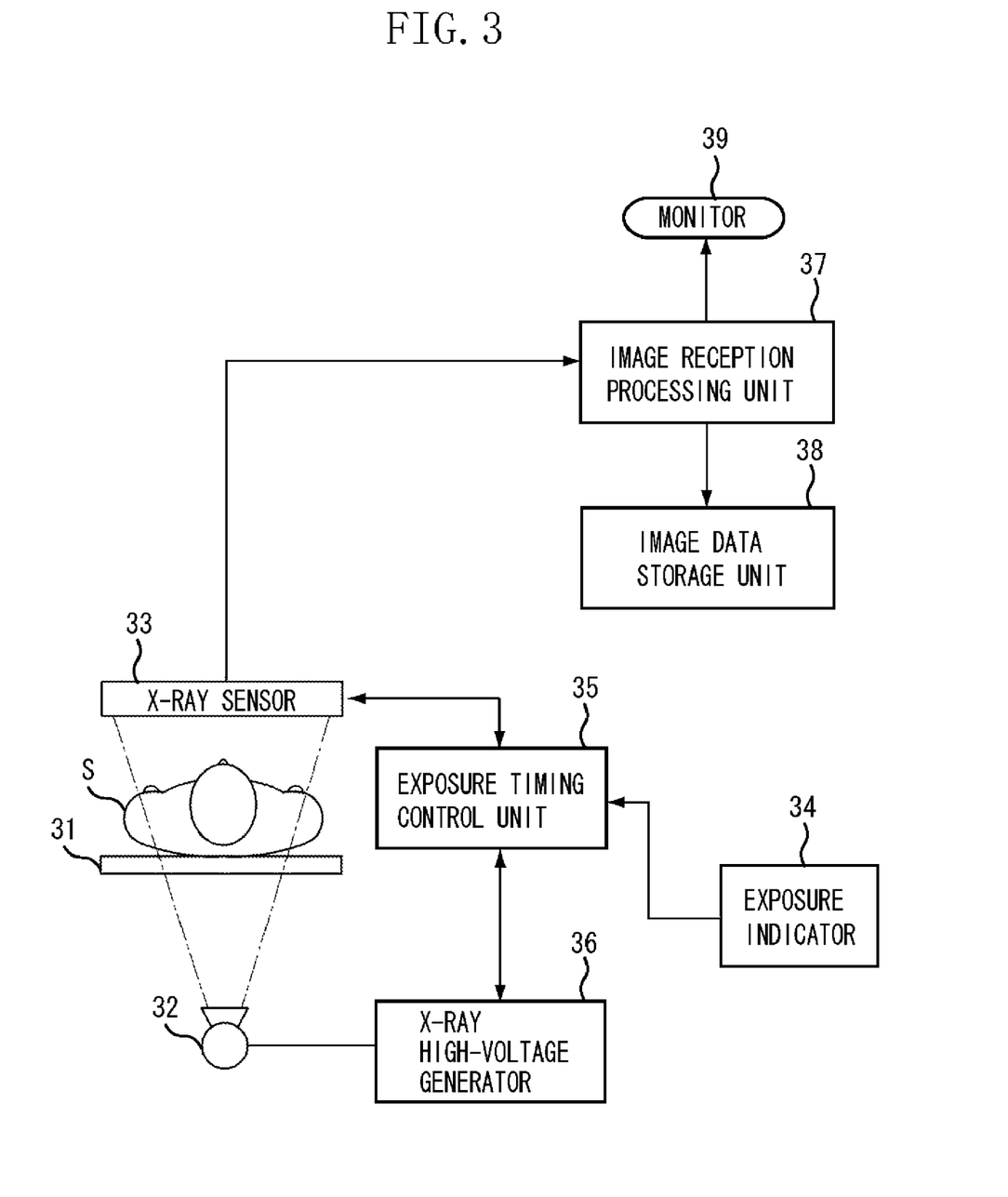
FIG. 3 is a block circuit diagram of an X-ray imaging apparatus.

FIG. 3 is a block circuit diagram mainly illustrating the X-ray imaging unit 2 in the X-ray imaging apparatus. An X-ray tube 32 and an X-ray sensor 33 are respectively arranged above and below an object S on a table 31. An output of an exposure indicator 34 is connected to an exposure timing control unit 35. An output of the exposure timing control unit 35 is connected to the X-ray sensor 33 and is also connected to the X-ray tube 32 via an X-ray high-voltage generator 36.

Furthermore, an output of the X-ray sensor 33 is connected to an image reception processing unit 37. The imaging reception processing unit 37 is connected to an image data storage unit 38 and a monitor 39.

Figure 4:
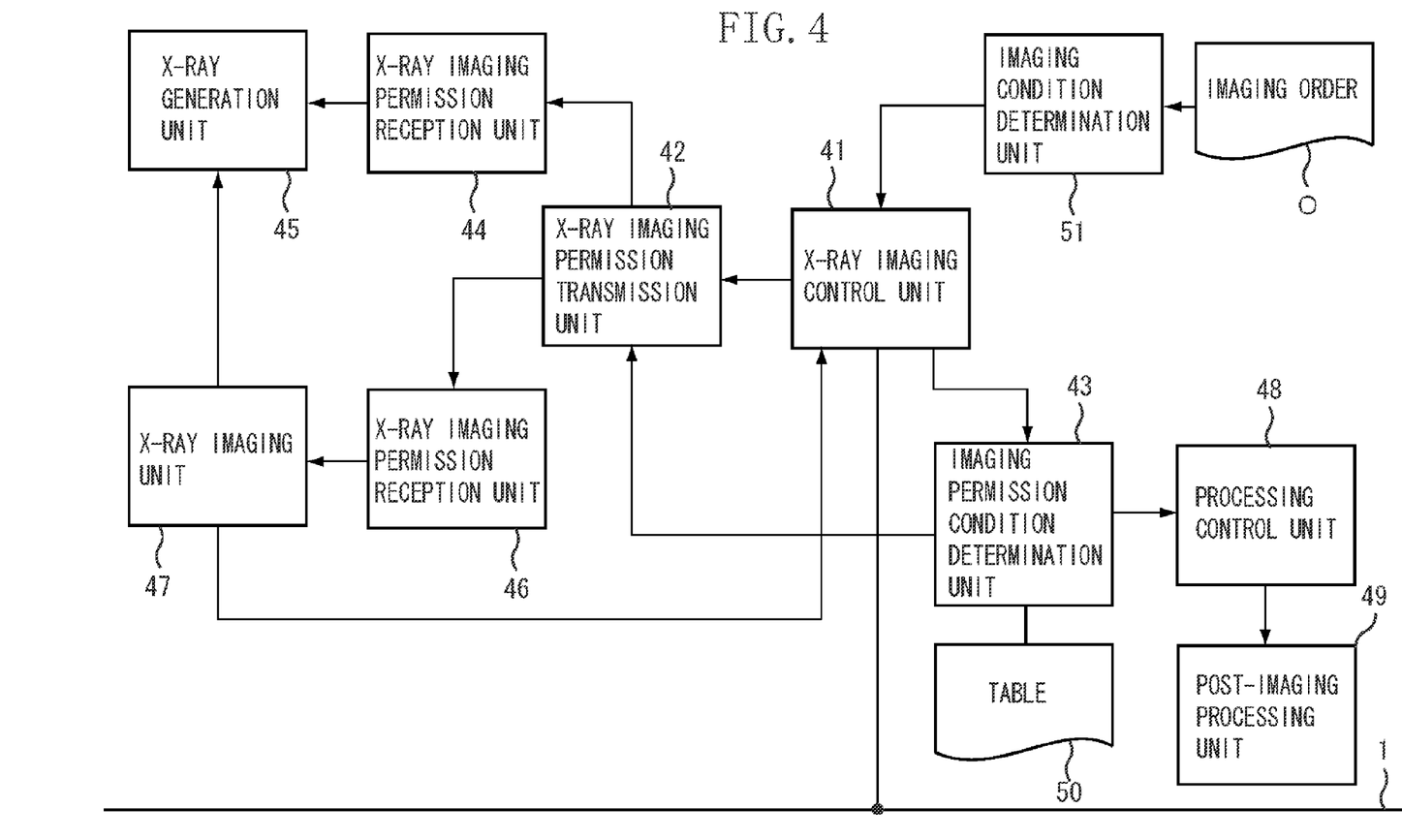
FIG. 4 is a functional block diagram of the X-ray imaging apparatus.

FIG. 4 is a functional block diagram of the X-ray imaging apparatus. An output of an X-ray imaging control unit 41 connected to the network 1 is connected to an X-ray imaging permission transmission unit 42 and an imaging permission condition determination unit 43.

An output of the X-ray imaging permission transmission unit 42 is connected to an X-ray generation unit 45 via an X-ray imaging permission reception unit 44 and is connected to the X-ray generation unit 45 via an X-ray imaging permission reception unit 46 and an X-ray imaging unit 47. An output of the X-ray imaging unit 47 is connected to the X-ray imaging control unit 41.

Furthermore, an output of the imaging permission condition determination unit 43 is connected to the X-ray imaging permission transmission unit 42 and is connected to a post-imaging processing unit 49 via a processing control unit 48. The imaging permission condition determination unit 43 is connected to a table 50. An instruction by an imaging order O is connected to the X-ray imaging control unit 41 via an imaging condition determination unit 51.

Figure 5:
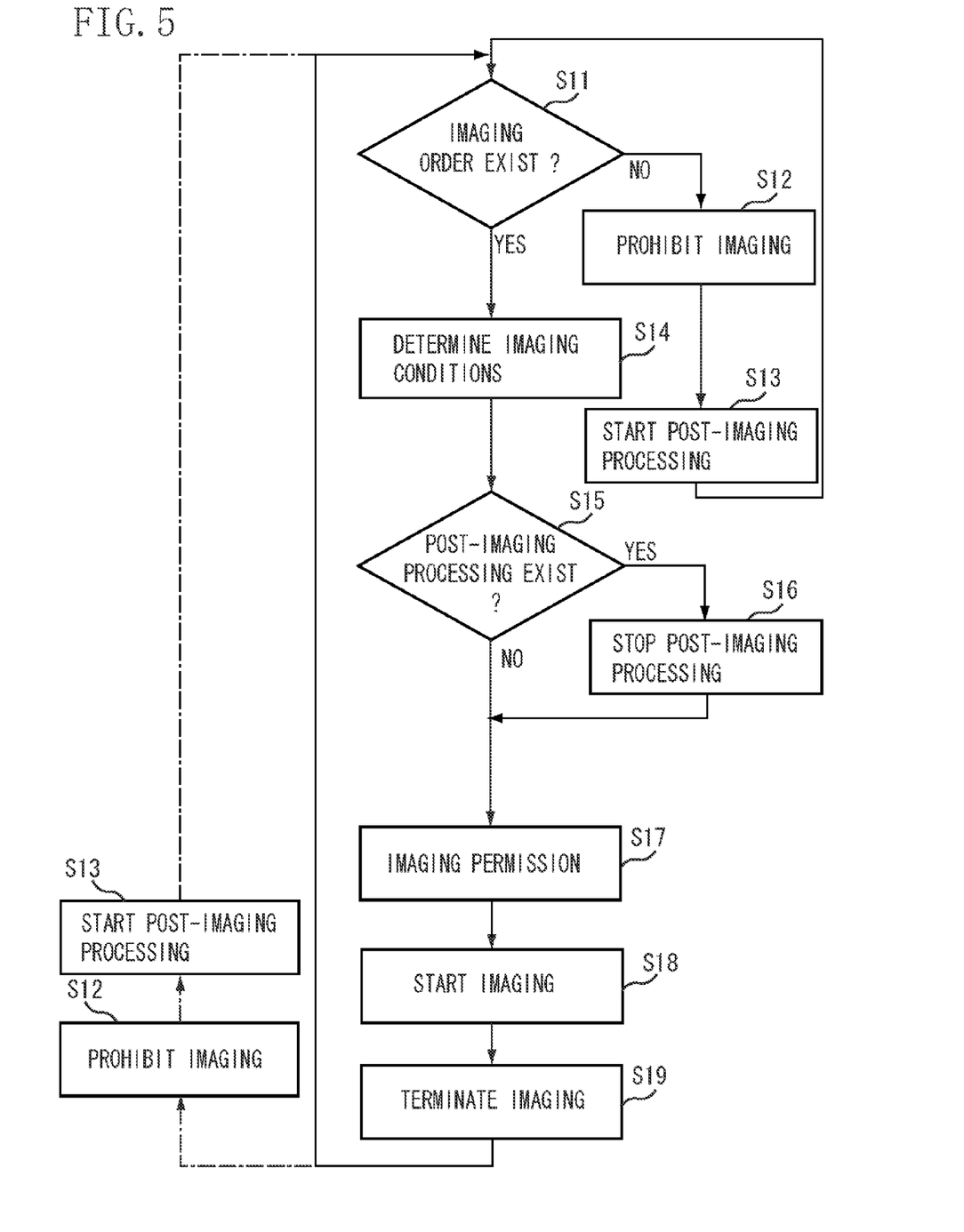
FIG. 5 is an operation flowchart according to the first exemplary embodiment.

FIG. 5 is an operation flowchart according to the present exemplary embodiment. In step S11, the X-ray imaging control unit 41 first checks the imaging order O received from an outside apparatus via the network 1. Alternatively, the X-ray imaging control unit 41 can also manually input or set the imaging order O. If the imaging order O exists (YES in step S11), the processing proceeds to step S14. Otherwise (NO in step S11), the processing proceeds to step S12.

In step S12, the X-ray imaging control unit 41 prohibits, when imaging is permitted, the imaging, to notify the two X-ray imaging permission reception units 44 and 46 of the prohibition of the imaging via the X-ray imaging permission transmission unit 42.

In step S13, the X-ray imaging control unit 41 starts post-imaging processing, or resumes, if there is post-imaging processing that has been stopped, the post-imaging processing. The post-imaging processing has a queue structure, and processing existing in a queue is performed successively. Therefore, a queue in which post-imaging processing is stopped is stored as it is as a post-processing queue. A processing thread or a processing process acquires the subsequent processing queue to perform processing.

Although in the present explanatory embodiment, the post-imaging processing is resumed after the imaging order O is checked, an instruction to start the post-imaging processing is not limited to this. More specifically, the instruction may be controlled so that the post-imaging processing is not performed while imaging is permitted. The post-imaging processing can be safely started upon completion of examination. The post-imaging processing may be performed when an operation unrelated to imaging, such as input of patient information, is being performed.

The imaging order O may require one or more imaging conditions at one time. In this case, a processing step relating to resumption of post-imaging processing may be carried out at the time point of completion of all imaging, and a processing step relating to resumption of post-imaging processing may be carried out during a pause in imaging.

When post-imaging processing is resumed during a pause in imaging, the processing for prohibiting the imaging in step S12 and the processing for starting the post-imaging processing in step S13 in flow indicated by a dot-dash line are performed after completion of imaging in step S19.

If the imaging order O exists (YES in step S11), then in step S14, the imaging condition determination unit 51 determines imaging conditions according to the imaging order O. The imaging conditions are determined by imaging order information, and can specify information relating to imaging, such as an imaging method, an imaging site, an imaging posture, an imaging direction, an imaging mode, an X-ray exposure condition, and an output destination.

The imaging mode specified by the imaging conditions include radioscopy, cineradiography, still image pickup, digital subtraction angiography (DSA), road map imaging, program imaging, tomography, and tomosynthesis imaging, which an X-ray imaging unit generally performs.

In each of the imaging modes, information relating to imaging, such as an imaging frame rate, an X-ray tube voltage, an X-ray tube current, a sensor reading area, sensor driving binning setting, collimator diaphragm setting, auto dose control (ADC), auto exposure control (AEC), and an X-ray window width, is specified.

In step S15, the X-ray imaging control unit 41 then checks the state of the post-imaging processing. The processing control unit 48 manages the contents of the post-imaging processing, and the post-imaging processing unit 49 performs the post-imaging processing. The "post-imaging processing" includes printing processing for printing a picked-up image on a film or paper, processing for transferring an image to an image server or an image viewer, and processing for storing an image in a local hard disk.

Examples of the type of post-imaging processing include Digital Imaging and Communications in Medicine (DICOM) storage transfer, DICOM print transfer, storage commit processing, modality performed procedure step (MPPS) processing, grayscale softcopy presentation state (GSPS) object generation processing, DICOM disk storage, image processing, and storage processing.

As a result of checking the post-imaging processing, if the post-imaging processing exists (YES in step S15), the processing proceeds to step S16. Otherwise (NO in step S15), the processing proceeds to step S17. Generally, communication conforming to a DICOM protocol serving as a standard for a communication line is established for the X-ray medical image.

In step S16, the X-ray imaging control unit 41 stops the post-imaging processing. If an imaging permission condition determined by the imaging permission condition determination unit 43 is the stop of post-imaging processing, the post-imaging processing performed by the post-imaging processing unit 49 is stopped via the processing control unit 48.

There are at least two types of methods to stop the post-imaging processing. The first method is to stop all the post-imaging processing currently being performed and the post-imaging processing scheduled to be performed in the future. The second method is to continue the post-imaging processing currently being performed, while stopping starting the post-imaging processing scheduled to be performed in the future.

Therefore, the processing for starting the post-imaging processing in step S13 requires processing for resuming the post-imaging processing currently being performed, which is forcedly terminated, and processing for starting the post-imaging processing scheduled to be performed.

In step S17, the X-ray imaging control unit 41 outputs imaging permission. The X-ray imaging control unit 41 notifies, if the imaging permission condition determined by the imaging permission condition determination unit 43 is the permission of imaging, the X-ray imaging permission reception units 44 and 46 of the imaging permission via the X-ray imaging permission transmission unit 42.

The imaging permission condition satisfies the imaging permission condition determined by the imaging permission condition determination unit 43. When the imaging permission condition determined by the imaging permission condition determination unit 43 is the stop of all post-imaging processing, the imaging permission can be given if it is confirmed that all the post-imaging processing is stopped.

When the imaging permission condition is a condition under that post-imaging processing currently being performed is normally terminated and post-imaging processing scheduled to be performed in the future is not started, the post-imaging processing scheduled to be performed in the future is stopped so as not to be started, and the imaging is permitted upon completion of the post-imaging processing currently being performed.

When the imaging may be permitted without waiting for the completion of the post-imaging processing currently being performed, the imaging may be permitted at the time point where the post-imaging processing scheduled to be performed in the future is stopped so as not to be started. When the above-mentioned imaging permission condition is satisfied, the X-ray imaging control unit 41 notifies the X-ray generation unit 45 and the X-ray imaging unit 47 of the imaging permission.

In step S18, the X-ray imaging control unit 41 then performs the imaging. The X-ray imaging unit 47 images X-rays exposed by the X-ray generation unit 45, to collect an X-ray image. The collected X-ray image is transferred to the X-ray imaging control unit 41.

In the imaging reception processing unit 37 in the X-ray imaging control unit 41, image reception processing, image processing, image display, and image storage are performed. In the image processing, known recursive filter processing, known noise reduction processing, known geometric conversion processing (rotation, enlargement, contraction, right/left inversion, top/bottom inversion, movement), and gradation conversion processing (a contrast ratio, black/white inversion) are performed. The image data storage unit 38 stores an image in the memory 13 or the image storage unit 20.

In step S19, the X-ray imaging control unit 41 then terminates the imaging. X-ray imaging is terminated upon completion of image transfer from the X-ray imaging unit 47 to the X-ray imaging control unit 41. Alternatively, X-ray imaging is terminated by giving end notification from the X-ray imaging unit 47.

When the post-imaging processing is resumed during a pause in imaging, the processing for prohibiting the imaging permission in step S12 and the processing for starting the post-imaging processing in step S13 are performed. If the post-imaging processing is resumed at the time point of completion of all the imaging, the processing proceeds to step S11.

In the present exemplary embodiment, the post-imaging processing is controlled using the imaging order information, to prepare for the imaging processing. Therefore, the X-ray imaging apparatus can be brought into an imaging wait state where real time processing is guaranteed prior to imaging. This enables a real time processing resource to be acquired at the start of the imaging more reliably than carrying out various types of processing control since the start of the imaging.

Figure 6:
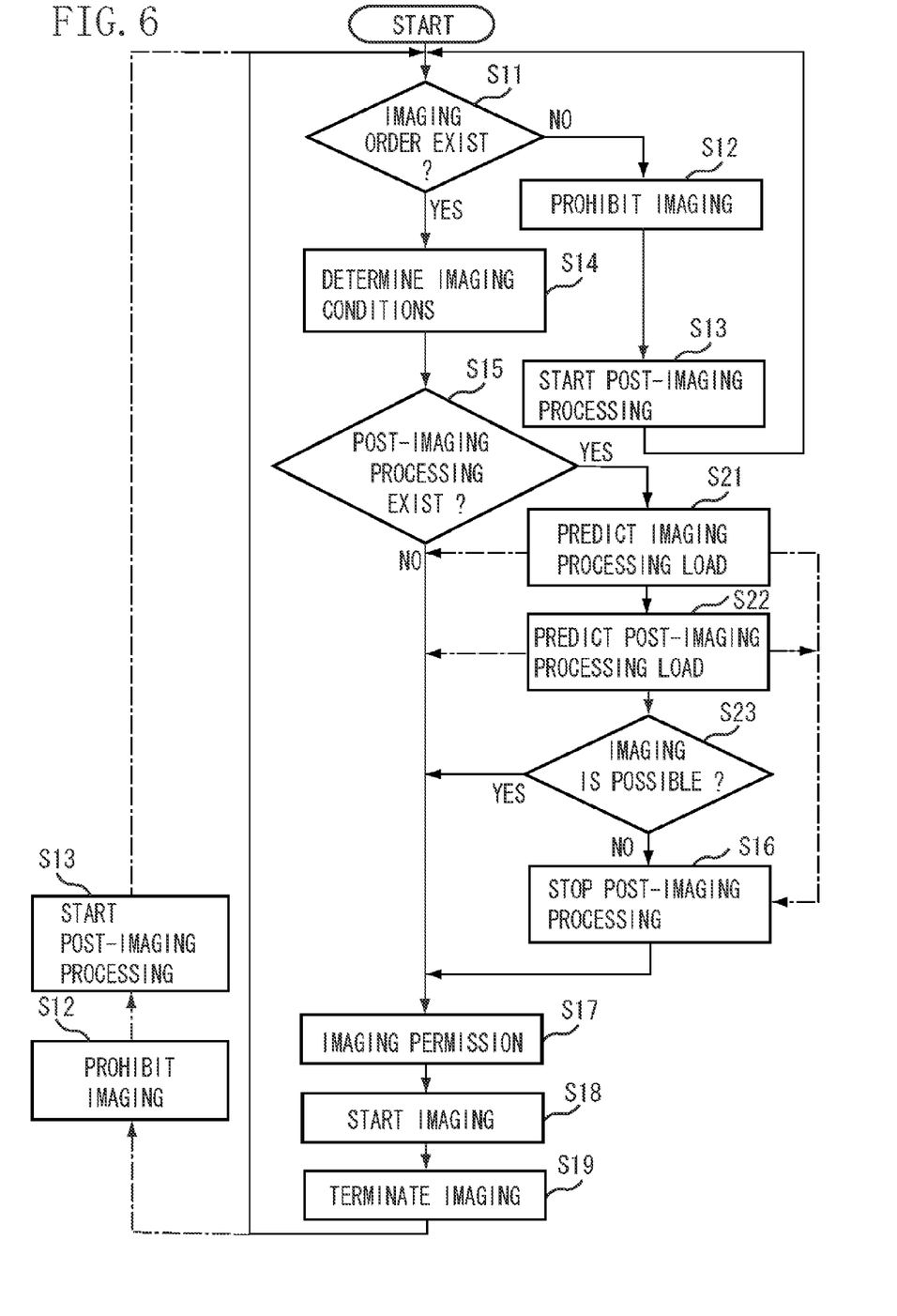
FIG. 6 is an operation flowchart according to a second exemplary embodiment.

FIG. 6 is an operation flowchart according to a second exemplary embodiment. In FIG. 6, the processes with the same step numbers as the step numbers illustrated in FIG. 5 perform similar processing.

In step S15, an X-ray imaging control unit 41 checks the state of post-imaging processing. If there is post-imaging processing (YES in step S15), the processing proceeds to step S21. Otherwise (NO in step S15), the processing proceeds to step S17. In step S21, the X-ray imaging control unit 41 predicts an imaging processing load. The imaging processing load is managed by a setting table.

Figure 7A:
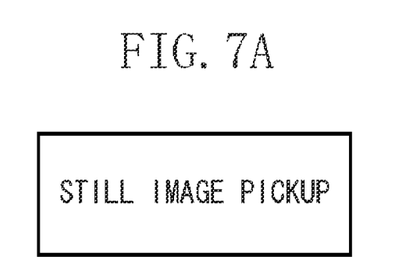
FIGS. 7A, 7B, 7C, and 7D are respectively tables for predicting an imaging processing load from an imaging order.
Figure 7B:
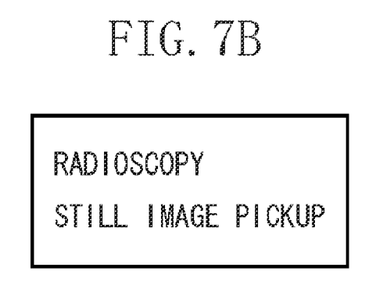
Figure 7C:
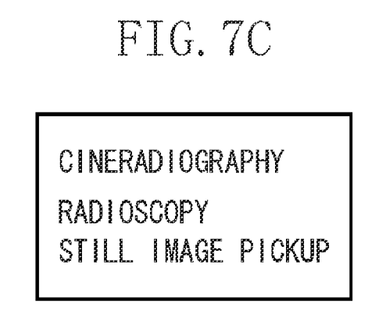

FIGS. 7A to 7C respectively illustrate tables for predicting an imaging processing load by an imaging order O determined in step S11. FIGS. 7A to 7C respectively illustrate examples of the imaging order O, where FIG. 7A illustrates an imaging order O for performing only still image pickup, FIG. 7B illustrates an imaging order O for performing radioscopy and still image pickup, and FIG. 7C illustrates an imaging order O for performing cineradiography, radioscopy, and still image pickup.

Figure 7D:
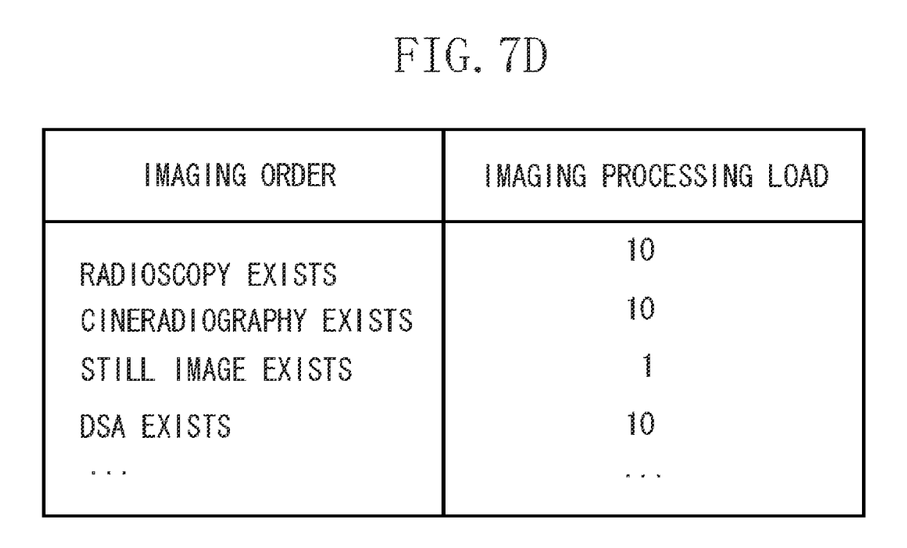

For the imaging orders O, an imaging processing load is managed depending on the presence or absence of an imaging mode within each of the imaging orders O in the setting table illustrated in FIG. 7D. In this example, if there is radioscopy within the imaging order O, the imaging processing load is set to ten at that time point.

Although the imaging processing load is set to ten, assuming that ten is its maximum value, this numerical value can be changed and is not limited to this. The above-mentioned processing enables preparation for imaging immediately at the time point of acceptance of the imaging order O.

Figure 8:
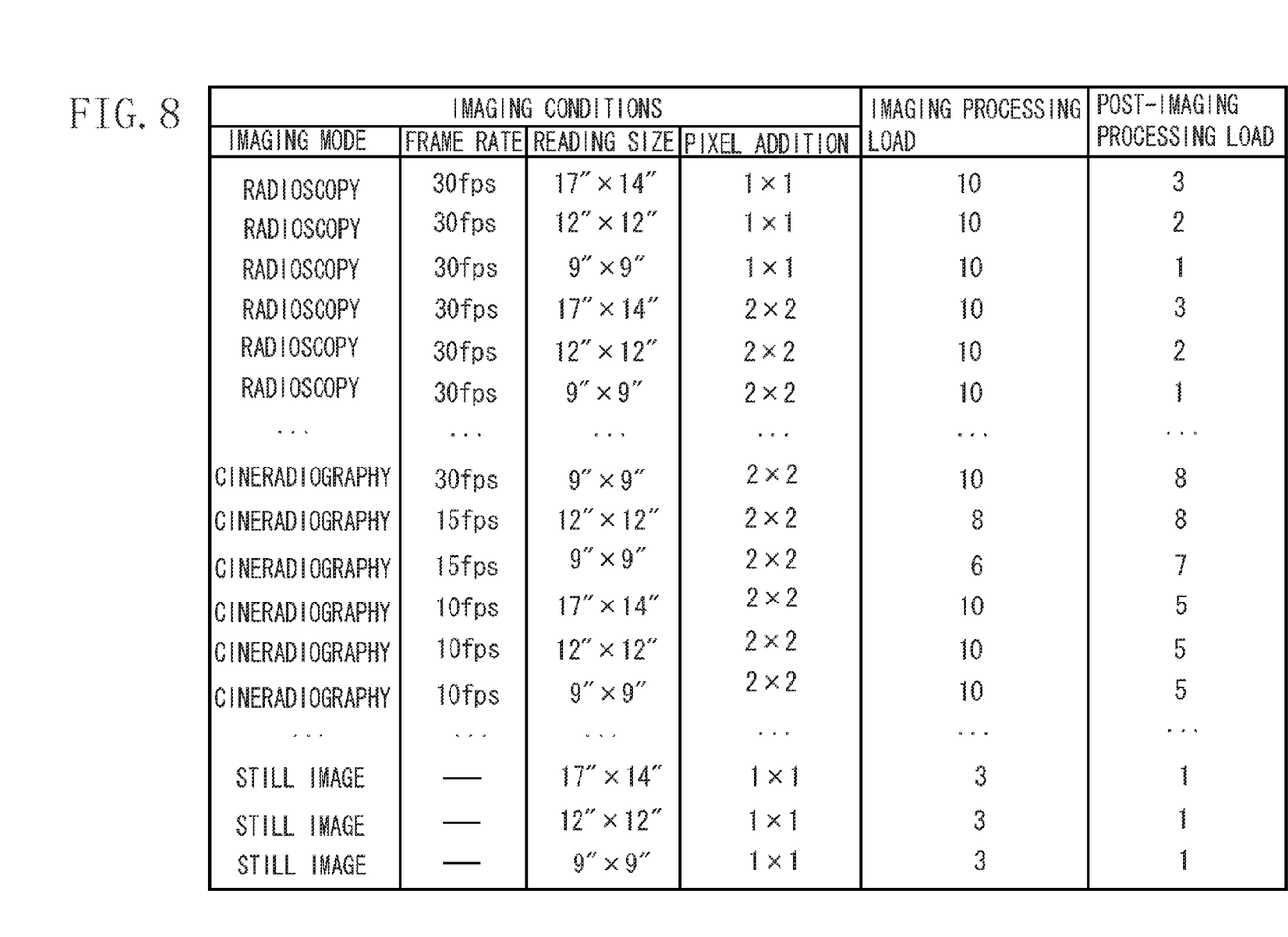
FIG. 8 is a table for predicting an imaging processing load and a post-imaging processing load from imaging conditions.

On the other hand, FIG. 8 illustrates a table for predicting an imaging processing load obtained from the imaging conditions determined in step S14. In this example, predicted values are set depending on various types of imaging conditions. Although the table manages an imaging processing load according to the imaging conditions such as a radioscopic mode, a frame rate, a reading size, and pixel addition, imaging processing conditions (not illustrated) may be considered in addition thereto.

In this example, the imaging processing load is ten when the imaging mode is radioscopy, the frame rate is 30 fps, the reading size is 9"×9", and the pixel addition condition is 2×2. Although the imaging processing load is set to ten, assuming that ten is its maximum value, this numerical value can be changed and is not limited to this.

Figure 9A:
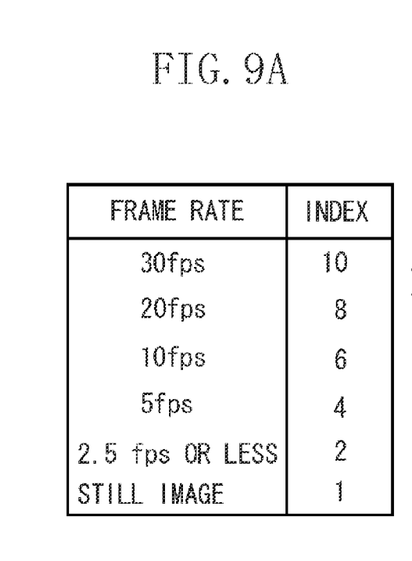
FIGS. 9A, 9B, and 9C are respectively tables for predicting an imaging processing load from imaging conditions.
Figure 9B:
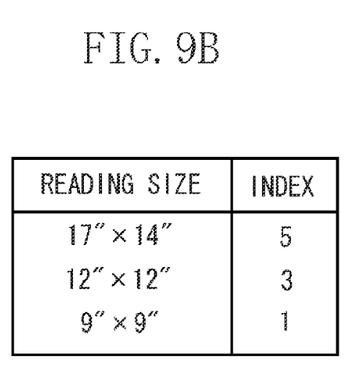
Figure 9C:
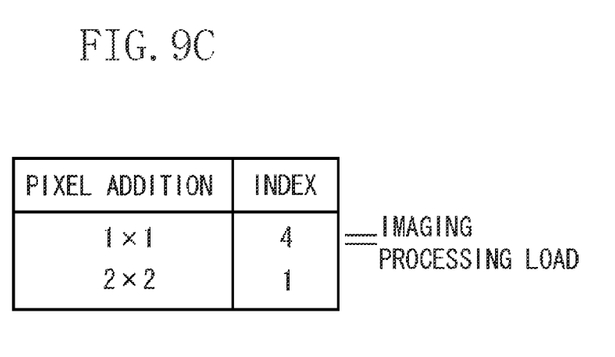

FIGS. 9A, 9B, and 9C respectively illustrate tables for predicting an imaging processing load obtained from the imaging conditions determined in step S14. In this example, an index table is prepared for each of items of the imaging conditions, and an imaging processing load is predicted by multiplication of the index tables.

FIG. 9A illustrates a table for managing a processing load index by a frame rate. If the frame rate is 30 fps, for example, the processing load index is ten. Although the imaging processing load is predicted using the multiplication of the index tables for the items, not the multiplication but addition may be used. Alternatively, a combination of the multiplication and the addition may be used.

Numerical values illustrated in FIGS. 9A, 9B, and 9C are not limited to these. When the result of calculation of the imaging processing load exceeds a threshold value, rounding-down processing can be safely performed. More specifically, assuming that the maximum imaging processing load is ten, the result of calculation of the imaging processing load is taken as ten if it exceeds ten.

In step S21, the X-ray imaging control unit 41 thus predicts the imaging processing load. When the imaging processing load is determined to be sufficiently high when predicted, processing in steps S22 and S23 can be also skipped. If the upper limit threshold value of the imaging processing load is set to nine, for example, processing for stopping post-imaging processing in step S16 can be also performed immediately at the time point where the predicted imaging processing load is nine or more.

Similarly, if the imaging processing load is determined to be sufficiently low when predicted, the processing may proceed to step S17. If the lower limit threshold value of the imaging processing load is set to two, for example, imaging permission in step S17 can be also given immediately at the time point where the predicted imaging processing load is two or less.

In step S22, the X-ray imaging control unit 41 then predicts a post-imaging processing load. The post-imaging processing load is managed by a setting table.

Figure 10A:
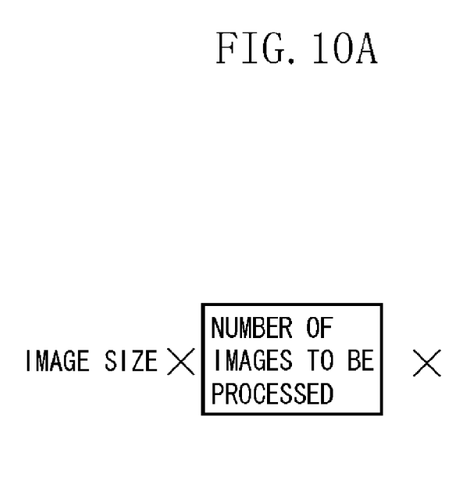
FIGS. 10A and 10B are respectively tables for predicting a post-imaging processing load from imaging data.
Figure 10B:
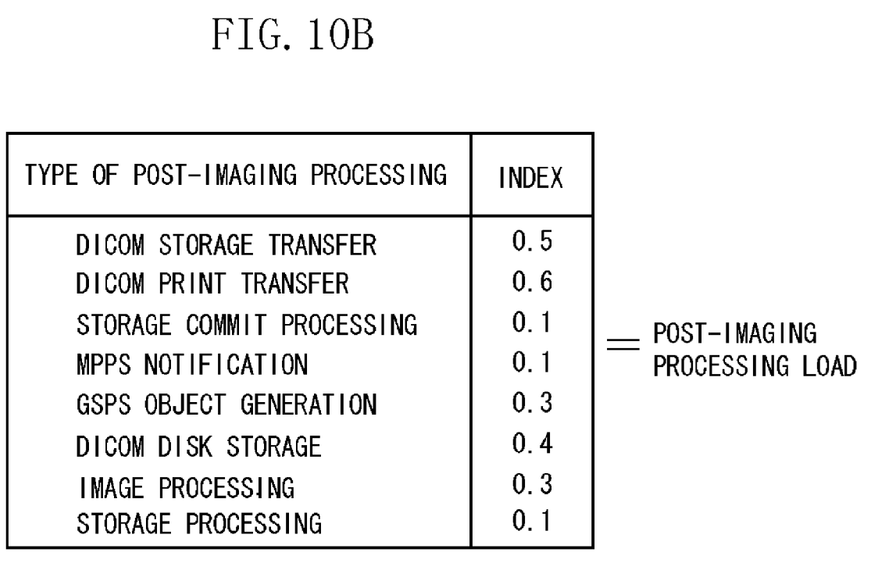

FIGS. 10A and 10B respectively illustrate examples of a table for predicting a post-imaging processing load, which is created based on the result of receiving imaging data obtained by imaging in steps S18 and S19 illustrated in FIG. 5 by an imaging reception processing unit 37. FIG. 10A illustrates the number of images to be post-processed in the imaging data of the result of the imaging. FIG. 10B illustrates a table describing an allowable threshold value of a processing load index managed for each type of post-imaging processing. If the type of post-imaging processing is DICOM print processing, for example, the processing load index is 0.6.

In this example, the post-imaging processing load is predicted using multiplication of the image size, the number of images to be processed, and the type of post-imaging processing. However, not the multiplication but addition may be used. Alternatively, a combination of the multiplication and the addition may be used. Numerical values illustrated in FIGS. 10A and 10B are not limited to these.

The post-imaging processing load is thus obtained in step S22. However, more than one post-imaging processing may exist. Therefore, post-imaging processing loads are respectively predicted for post-imaging processing currently being performed, and/or post-imaging processing scheduled to be then performed, and/or post-imaging processing scheduled to be performed within a predetermined time period, and/or all post-imaging processing.

If the post-imaging processing load is determined to be sufficiently higher than an allowable range when predicted, the processing in step S23 may be skipped. If the upper limit threshold value of the post-imaging processing load is set to 20, for example, the processing for stopping the post-imaging processing in step S16 can be also performed immediately at the time point where the predicted post-imaging processing load is 20 or more.

Similarly, if the predicted post-imaging processing load is determined to be sufficiently low when predicted, the processing may proceed to step S17. If the lower limit threshold value of the post-imaging processing load is set to two, for example, the imaging permission in step S17 may be also given immediately at the time point where the predicted post-imaging processing load is two or less.

Figure 11:
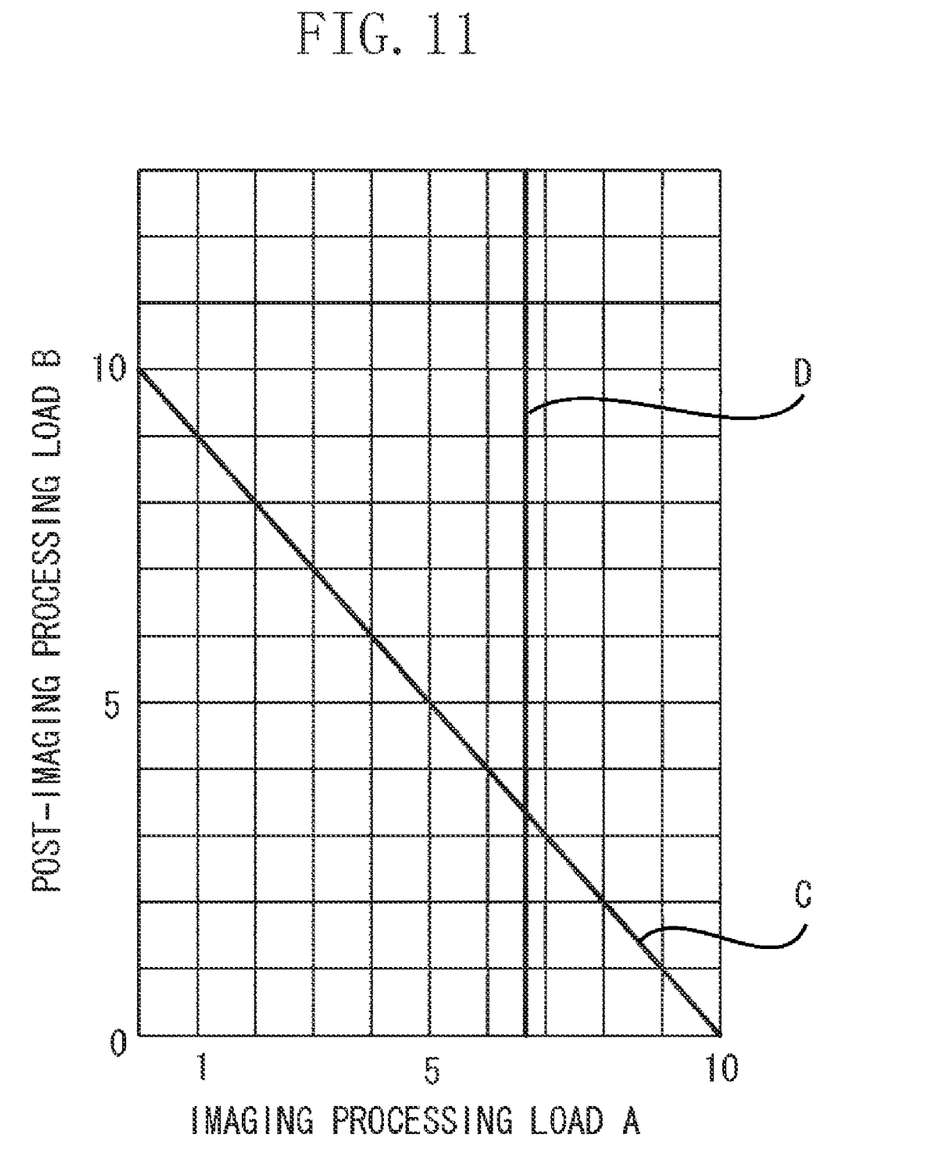
FIG. 11 is a graph for determining a processing load.

In step S23, the X-ray imaging control unit 41 then determines the imaging processing load predicted in step S21 and the post-imaging processing load predicted in step S22. FIG. 11 illustrates an example of the determination. In FIG. 11, an imaging processing load A predicted in step S21 is used as the horizontal axis, and a post-imaging processing load B predicted in step S22 is used as the vertical axis.

In FIG. 11, assuming that a processing load threshold value is C, when the predicted processing load is in an area below the threshold value C, it is determined that imaging is possible (Yes in step S23), and the processing proceeds to step S17.

On the other hand, when the predicted processing load is in an area above the threshold value C, it is determined that imaging is impossible (No in step S23), and the processing proceeds to step S16. Furthermore, examples of the processing in step S16 include a method for immediately stopping post-imaging processing currently being performed and a method for stopping all post-imaging processing scheduled to be performed in the future.

When the imaging processing load A is higher than a threshold value D for determining the stop of processing in FIG. 11, the post-imaging processing currently being performed can be also immediately stopped. Although the threshold value D is around 6.8 in FIG. 11, the present invention is not limited to this value.

Processing subsequent to the processing in steps S16 and S17 is similar to that in the first exemplary embodiment.

In the second exemplary embodiment, the processing load is determined in step S23, and the imaging processing load A and the post-imaging processing load B are predicted in steps S21 and S22.

When the predicted processing load narrowly falls in the area above the processing load threshold value C illustrated in FIG. 11 in the present exemplary embodiment, if the predicted processing load falls in the area below the processing load threshold value C by slightly changing imaging conditions such as a frame rate, a reading size, and pixel addition, the imaging conditions are changed to permit imaging.

Furthermore, imaging permission can be outputted when a difference from the processing load threshold value C is within an allowable load threshold value. More specifically, when the predicted processing load narrowly falls in the area above the threshold value C, if the difference from the threshold value C falls in the allowable load threshold value, imaging permission is outputted. The allowable load threshold value may be any value, or may be held as a table. When the allowable load threshold value is held as a table, the threshold value is set depending on the imaging processing load A and the post-imaging processing load B.

When imaging is continued for a long time under such circumstances that too much preference is given to imaging processing over post-imaging processing, post-imaging processing may not be performed, and computer resources may be used too much. When such a system configuration in which images to be post-imaging processed are stored on a memory is employed, for example, a memory resource may be consumed continuously.

If imaging itself is prevented in such a case, imaging may be impossible when required by a user. In order to prevent imaging from being impossible, therefore, imaging conditions can be also changed if a difference from a threshold value can be less than an allowable load threshold value by changing imaging conditions.

A computer resource such as a memory may be consumed by continuing to stop post-imaging processing. Even in such a case, imaging is not prevented by changing imaging conditions. Therefore, a minimum of imaging can be performed when required by a user.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-279827 filed Oct. 30, 2008, which is hereby incorporated by reference herein in its entirety.

What is claimed is:

1. An X-ray imaging apparatus including an X-ray imaging unit configured to acquire an X-ray image by imaging using X-rays generated by an X-ray generation unit, the X-ray imaging apparatus comprising:
a post-imaging processing unit configured to perform post-imaging processing for the X-ray image acquired by the X-ray imaging unit;
a determination unit configured to determine in real time whether an imaging order for the X-ray image is received; and
a control unit configured to cause the post-imaging processing unit to perform the post-imaging processing when the determination unit does not determine that the imaging order for the X-ray image is received, while causing the post-imaging processing unit to stop the post-imaging processing and then permitting the imaging of the X-rays by the imaging order when the determination unit determines that the imaging order for the X-ray image is received and the post-imaging processing unit is performing the post-imaging processing.

2. An X-ray imaging apparatus configured to capture a medical X-ray image by communicating information among an X-ray generation unit configured to generate X-rays, an X-ray imaging unit configured to perform X-ray imaging, and an X-ray imaging control unit configured to control X-ray imaging via a communication line,
wherein
the X-ray generation unit includes an X-ray imaging permission reception unit configured to receive X-ray imaging permission from the X-ray imaging control unit, and
the X-ray imaging unit includes an X-ray imaging permission reception unit configured to receive the X-ray imaging permission from the X-ray imaging control unit, and
the X-ray imaging control unit includes an X-ray imaging permission transmission unit configured to transmit the X-ray imaging permission to the X-ray generation unit and the X-ray imaging unit, an imaging condition determination unit configured to determine an imaging condition from an imaging order, an imaging permission condition determination unit configured to determine an imaging permission condition from the imaging condition determined by the imaging condition determination unit, and a processing control unit configured to perform processing according to the imaging permission condition determined by the imaging permission condition determination unit.

3. The X-ray imaging apparatus according to claim 2, wherein the imaging permission condition determination unit stops the processing performed by the X-ray imaging control unit, to permit the imaging.

4. The X-ray imaging apparatus according to claim 2, wherein the imaging permission condition determination unit stops, when the X-ray imaging control unit performs more than one processing, starting the subsequent processing, and determines the permission of the imaging upon completion of the processing currently being performed.

5. The X-ray imaging apparatus according to claim 2, wherein the imaging permission condition determination unit determines the permission of the imaging by a processing load predicted when the imaging is performed under the imaging condition determined by the imaging condition determination unit or the predicted processing load for the processing to be performed by the X-ray imaging control unit.

6. The X-ray imaging apparatus according to claim 5, wherein the imaging permission condition determination unit determines the permission of the imaging if the processing load predicted when the imaging is performed under the imaging condition determined by the imaging condition determination unit or the predicted processing load for the processing to be performed by the X-ray imaging control unit falls in an allowable range.

7. The X-ray imaging apparatus according to claim 6, wherein the imaging permission condition determination unit determines the permission of the imaging by changing the imaging condition determined by the imaging condition determination unit such that the processing load predicted when the imaging is performed under the imaging condition or the predicted processing load for the processing performed by the X-ray imaging control unit falls in the allowable range.

8. The X-ray imaging apparatus according to claim 2, wherein the imaging permission condition determination unit determines the imaging permission condition based on a table describing an allowable threshold value of a predicted processing load or a processing load.

9. The X-ray imaging apparatus according to claim 8, wherein the table is a table of the imaging order and an imaging processing load.

10. The X-ray imaging apparatus according to claim 8, wherein the table is a table of imaging conditions, an imaging processing load and/or a post-imaging processing load.

11. The X-ray imaging apparatus according to claim 8, wherein the table is a table of a frame rate, a reading size, and pixel addition.

12. The X-ray imaging apparatus according to claim 8, wherein the table is a table of the type of post-imaging processing, and the type of post-imaging processing is any one of DICOM storage transfer, DICOM print transfer, storage commit processing, MPPS processing, GSPS object generation processing, DICOM disk storage, image processing, and storage processing.

13. The X-ray imaging apparatus according to claim 2, wherein the imaging permission condition determination unit starts the processing to be performed in the X-ray imaging unit, which has been stopped when the imaging condition determination unit has not determined the imaging condition.

14. The X-ray imaging apparatus according to claim 2, wherein the imaging permission condition determination unit starts the processing to be performed in the X-ray imaging unit, which has been stopped, at the time point of completion of the imaging.

15. An X-ray imaging method comprising:

performing post-imaging processing for an X-ray image acquired by imaging using generated X-rays;

determining in real time whether an imaging order for the X-ray image is received;

performing the post-imaging processing when it is not determined that the imaging order for the X-ray image is received, while stopping the post-imaging processing and then permitting the imaging of the X-rays by the imaging order when it is determined that the imaging order for the X-ray image is received and the post-imaging processing is being performed.

16. A computer readable medium storing a computer program of instructions which cause the computer to perform an X-ray imaging method, the method comprising:

performing post-imaging processing for an X-ray image acquired by imaging using generated X-rays;

determining in real time whether an imaging order of the X-ray image is received;

performing the post-imaging processing when it is not determined that the imaging order of the X-ray image is received, while stopping the post-imaging processing and then permitting the imaging of the X-rays by the imaging order when it is determined that the imaging order of the X-ray image is received and the post-imaging processing is being performed.

* * * * *